United States Patent
Ciesla et al.

(10) Patent No.: US 6,865,014 B2
(45) Date of Patent: Mar. 8, 2005

(54) APPARATUS AND METHOD FOR INVESTIGATING A SAMPLE

(75) Inventors: Craig Michael Ciesla, Cambridge (GB); Bryan Edward Cole, Cambridge (GB); Donald Dominic Arnone, Cambridge (GB)

(73) Assignee: Teraview Limited (GB)

( * ) Notice: Subject to any disclaimer, the term of this patent is extended or adjusted under 35 U.S.C. 154(b) by 85 days.

(21) Appl. No.: 10/240,341

(22) PCT Filed: Mar. 29, 2001

(86) PCT No.: PCT/GB01/01409

§ 371 (c)(1),
(2), (4) Date: Jan. 28, 2003

(87) PCT Pub. No.: WO01/75422

PCT Pub. Date: Oct. 11, 2001

(65) Prior Publication Data

US 2003/0165003 A1 Sep. 4, 2003

(30) Foreign Application Priority Data

Mar. 31, 2000 (GB) .............................................. 0007876

(51) Int. Cl.[7] .......................... G02F 1/355; G01N 21/17
(52) U.S. Cl. ........................ 359/326; 385/12; 356/436; 356/445
(58) Field of Search ............. 385/12–13; 359/326–332; 356/337, 338, 436, 440, 441, 442, 445

(56) References Cited

U.S. PATENT DOCUMENTS

| | | | |
|---|---|---|---|
| 4,253,766 A | * | 3/1981 | Funk ........................... 356/418 |
| 5,623,145 A | | 4/1997 | Nuss ........................... 250/330 |
| 5,625,459 A | | 4/1997 | Driver ......................... 356/446 |
| 5,650,856 A | * | 7/1997 | Morse .......................... 356/436 |
| 5,710,430 A | | 1/1998 | Nuss ......................... 250/358.1 |
| 5,911,017 A | | 6/1999 | Wach et al. ................... 385/12 |

FOREIGN PATENT DOCUMENTS

| | | |
|---|---|---|
| JP | 2000-352558 | 12/2000 |
| WO | WO 00/36399 | 6/2000 |
| WO | 00/36399 | 6/2000 |
| WO | WO 00/49447 | 8/2000 |
| WO | 00/49447 | 8/2000 |

OTHER PUBLICATIONS

Q. Wu, et al., "7 Terahertz Broadband Gap Electro–Optic Sensor", *Applied Physics Letters*, American Institute of Physics, vol. 70, No. 14, Apr. 7, 1997, pp. 1784–1786.

D.D. Arnone, et al., "Applications of Terahertz (THz) Technology to Medical Imaging", *Conference on Terahertz Spectroscopy and Applications II. SPIE*, vol. 3828, Jun. 1999, pp. 209–219.

Q. Wu, et al., "7 Terahertz Broadband Gap Electro–Optic–Sensor", Applied Physics Letters, American Institute of Physics, vol. 70, No. 14, Apr. 7, 1997, pp. 1784–1786.

(List continued on next page.)

*Primary Examiner*—John D. Lee
(74) *Attorney, Agent, or Firm*—Ostrolenk, Faber, Gerb & Soffen, LLP

(57) ABSTRACT

An apparatus for investigating a sample, the apparatus comprising an emitter (1) for irradiating the sample (27) with a beam of emitted electromagnetic radiation; and a detector (49) for detecting the radiation reflected from the sample, wherein there is an optically non-linear member (15) which functions as both an active part of the emitter and an active part of the detector, said emitter and detector using the same part of the optically non-linear member (15). The electromagnetic radiation is primarily intended to be in the terahertz (THz) frequency range.

20 Claims, 4 Drawing Sheets

OTHER PUBLICATIONS

R. Vonach et al., "Application of Mid–Infrared Transmission Spectrometry to the Direct Determination of Glucose in Whole Blood" Institute for Analytical Chemistry (No Date).

D. Venables et al., "Far–infrared Spectra and Associated Dynamic in Aotonitrile–Water Mixtures Measured With Femtosecond THz Pulse Spectroscopy" American Institute of Physics, Vo., 108, No. 12, Mar. 22, 1998, pp. 4935–4944, Journal of Chemical Physics.

J.E. Pedersen, et al., "THz Time–Domain Spectroscopy of Nonpolar Liquid" IEEE Journal of Quantum Electronics, vol. 28, No. 10, Oct. 1992, pp. 2518–2522.

G. Budinova et al., "Application of Molecular Spectroscopy In the Mid–Infrared Region to the Determination of Glucose and Cholesterol in Whole Blood and in Blood Serum", Abstract, Applied Spectroscopy, 2003.

Abstract of JP 2000/352558, T. Hironori "Teraherz Spectroscope", Dec. 19, 2000.

* cited by examiner

APPARATUS AND METHOD FOR INVESTIGATING A SAMPLE

The present invention relates to the field of apparatus and methods for investigating samples. More specifically, the present invention is concerned with the field of compact apparatus which can be used to analyse liquids, biological samples, semiconductors and other inorganic samples.

Recently, there has been considerable interest in investigating samples, by obtaining spectral data or images of the samples using radiation in the frequency range from about 25 GHz to 100 THz. Thus frequency range extends from the mid-infrared part of the electromagnetic spectra down to the microwave region and is colloquially referred to as "Terahertz" (THz) radiation.

There is no particularly efficient naturally occurring source of THz radiation. A particularly prevalent method for generating such radiation is to use a frequency conversion member which is configured to change the frequency of an input beam or pump beam. Such frequency conversion members are often optically non-linear members. These materials can also be used as an active part of a detector for THz radiation.

Previously, the Terahertz emitter and detector have been separately arranged. However, this leads to a needlessly bulky and complex arrangement.

Therefore, in a first aspect, the present invention provides an apparatus for investigating a sample, the apparatus comprising an emitter for irradiating the sample with a beam of emitted electromagnetic radiation; and a detector for detecting radiation reflected from the sample, wherein there is an optically non-linear member which functions as both an active part of the emitter and an active part of the detector, said emitter and detector using the same region of the optically non-linear member.

The apparatus according to a first aspect of the present invention are primarily intended for use using emitted radiation with a frequency in the THz frequency range i.e. from 25 GHz to 100 THz. However, it will be appreciated that the apparatus could be used with any type of radiation where an optically non-linear member is used to generate radiation of the desired frequency.

Preferably, the emitted beam is a pulsed beam comprising a plurality of different frequency components.

The non-linear member is configured to emit radiation in response to irradiation with one or more input beams or pump beams. The non-linear member is preferably is configured to emit a beam of radiation having a frequency which is the difference of two of the frequencies of the one or more pump beams. A single pump beam may have one or more frequency components For example, if the pump beam could be a pulsed beam.

Examples of suitable non-linear members are $NH_4H_2PO_4$, ADP, $KH_2PO_4$, $KH_2ASO_4$, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium). In general, non-centrosymmetric crystals are used for second order effects.

As mentioned above, the non-linear member is also used in the detector. Preferably, the detector operates using the AC pockels effect. In this is achieved using the AC Pockels effect. In this effect, the reflected THz radiation causes a temporary birefringence in the non-linear member which causes the rotation of the polarisation of another beam of a higher frequency. This other beam will be referred to as a "probe beam". Therefore, the information from the reflected THz radiation is encoded onto the probe beam. Typically, the probe beam and the THz radiation will be combined prior to entering the non-linear member.

The above list of typical materials which can be used for the frequency conversion member are also suitable for use as a detector.

Preferably, the probe beam is polarised before entering the non-linear member. More preferably, the probe beam is linearly polarised.

As the reflected THz radiation is used to induce birefringence in the frequency conversion member, the frequency conversion member preferably has negligible intrinsic birefringence. If the frequency conversion member has non-negligible birefringence, the probe beam can be pre-biased before entering the frequency conversion member to compensate for any change in the polarisation due to the intrinsic birefringence of the frequency conversion member.

As the same frequency conversion member is used for both emission and detection, there is a need to be able to distinguish between the emitted and reflected radiation. This can be done in a number of ways. However, a particularly preferable method is to use pulsed radiation. Typically radiation where the pulses are separated by greater than 10 ns are used so that the frequency conversion member does not emit and detect radiation at the same time.

Preferably, the pump beam and the probe beam are derived from the same source. In order to distinguish the radiation which has been reflected from the sample from spurious radiation form the pump beam/probe beam etc. Preferably, the pump beam and/or the probe beam are modulated with frequencies $f_1$ and $f_2$ respectively. The detector can then be configured to detect radiation which has a modulation frequency of $f_1-f_2$, or $f_1$ or $f_2$ etc.

More preferably, the present invention is provided with means to measure a reference signal, said means preferably comprises a mirror member which is partially reflective to the emitted radiation. The mirror member being located between the non-linear member and the sample. The THz radiation which is reflected from this partial reflector is then detected in the same way as the THz radiation which is reflected from the sample.

In order to distinguish between the radiation reflected from the sample and the radiation reflected from the reflector, the probe beam is preferably divided into two probe beams, a sample probe beam and a reference probe beam. The optical path of each of the probe beams being different and being configured such pulses from the sample probe beam reach the frequency conversion member with the THz pulses reflected from the sample, and that pulses from the reference probe beam reach the frequency conversion member with THz pulses which have been reflected from the THz reflector. Even more preferably, a different modulation frequency is applied to both of the probe beams.

The present invention can be used both for obtaining spectra of a sample and for imaging a sample.

In a second aspect, the present invention provides a method for investigating a sample, the method comprising the steps of irradiating a sample with a beam of emitted electromagnetic radiation which is emitted from a non-linear crystal; detecting the radiation which is reflected from the sample using the said non-linear crystal as an active part of the detector; wherein the steps of irradiating and detecting the reflected radiation use the same region of the non-linear crystal.

R. Vonach et al, Applied Spectroscopy, 52, 1998 p820–822 demonstrate that clinically important changes in the glucose level of human blood can be obtained from infrared spectra taken in the mid infra-red range and the high frequency THz range. Using this method a spectrum can be achieved within two minutes. However, THz spectroscopy is much faster and a spectra can be obtained in a little as 50 milliseconds.

An apparatus according to a first aspect of the present invention is preferably configured to obtain spectra from individual tests tubes in an assay tray. An assay tray being a tray having a two dimensional array of test tube holders. Of course, alternative sample holders to assay group may be used.

In a third aspect, the present invention provides an apparatus for analysing a plurality of individual liquid samples, the apparatus comprising:
means for holding the liquid samples which are to be analysed;
an emitter for irradiating at least one of the samples with a beam of radiation having a frequency in the range from 25 GHz to 100 THz; and
a detector for detecting radiation which is reflected from the at least one sample.

The plurality of liquids samples are preferably located in an assay tray.

The apparatus can be configured to sequentially sample a plurality of liquid samples, one after another. For example, the means for holding the sample could be connected to a stepper motor which would sequentially move the samples through the beam of pulsed THz radiation. Ideally, the sample holder could be moved so that each liquid sample irradiated by the emitted beam for the time required to measure the entire THz pulse. However, in practice, it may be preferable to take more than one spectra per sample.

THz radiation can be used to look at samples, such as blood, urine, saliva, amniotic fluid etc. to determine information about, for example, the level of cholesterol, glucose, urea, uric acid and triglycerides.

Preferably, the emitter and detector comprise a common non-linear member. This allows the size and the number of components in the system to be reduced.

In a fourth aspect, the present invention provides a method of analysing a plurality of liquid samples, the method comprising the steps of irradiating at least one liquid sample with a beam of pulsed electromagnetic radiation having a plurality of frequencies in the range from 25 GHz to 100 THz; detecting the radiation reflected from at least one sample.

The apparatus of the first aspect of the present invention can also be used to study bulk samples. An image of the sample can be obtained by stepping the sample relative to the emitted beam or the emitter and detector relative to the sample.

Reflection measurements ideally require the sample which is to be investigated to provide a flat surface to the incident radiation. If the surface of the sample is curved then the radiation will be reflected at an angle to the incident beam. This makes detection difficult.

Biological samples usually tend to be non-rigid, so, it is possible flatten the surface of the sample which receives the radiation, using a rigid member which is transparent to THz radiation. Preferably, to avoid any spurious reflections from the interface between the window and the sample, the refractive index of the window is chosen to substantially match the reflective index of the sample.

Therefore, in a fifth aspect, the present invention provides an apparatus for investigating a sample, the apparatus comprising: an emitter for irradiating the sample with a beam of emitted electromagnetic radiation; a detector for detecting radiation reflected from the sample; and a window member which is transparent to said emitted and reflected radiation, said window member having a refractive index which is substantially equal to that of the sample.

It is difficult to find a naturally occurring material which is both transparent to THz and which has a refractive index which is close to that of most biological materials, for example skin. Silicon grease is transparent to THz radiation. However, it does not have a particularly useful refractive index. However, the refractive index of the grease can be varied by forming a silicon colloid which comprises silicon particles in suspension within a silicon grease or germanium particles in suspension.

The present invention will now be described with reference to the following non-limiting embodiments in which.

Figure 1:
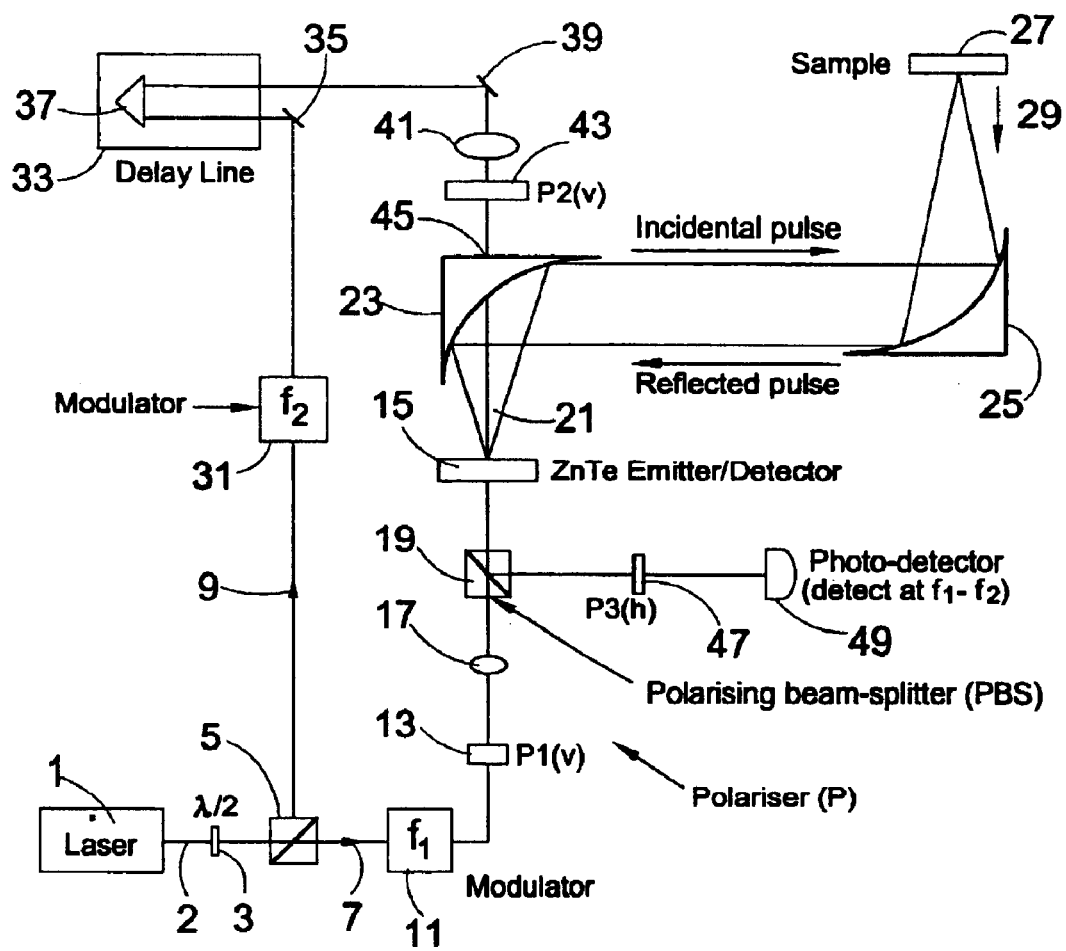
FIG. 1 shows a schematic apparatus in accordance with an embodiment of the present invention.

In the example of FIG. 1, laser 1 (which will be described in more detail with reference to FIG. 3) is configured to output a pulsed beam 2 having a wavelength of about 800 nm with a period of 10 fs. The beam is passed through halfwave plate 3 and onto polarising beam splitter 5. Beam splitter 5 divides the beam into a pump beam 7 which is used to generate THz radiation for imaging the sample and a probe beam 9 which is used to detect THz radiation reflected from the sample. The halfwave plate 3 is used to adjust the ratio of the intensity of the pump 7 and probe beams 9.

The pump 7 is first passed through an amplitude modulator 11. Modulator 11 is used to apply an amplitude modulation at frequency $f_1$ onto the pump beam 7. This modulation of the pump beam 7 is used to distinguish the pump beam during the detection process. The modulated pump beam 7 is then passed through first linear polariser 13 and is focused onto optically-non member 15 via lens 17. It will be recognised that polarisers are useful but not indispensable in many applications.

A polarising beam splitter 19 is provided in the path of the pump beam 7 between lens 17 and optically non-linear member 15.

Polarising beam splitter 19, is configured to freely allow the transmission of the pump beam 7 from lens 17 to the optically non-linear member 15.

Optically non-linear member 15 is configured to emit pulsed radiation with a plurality of frequencies, the frequencies which are the difference between the various frequency components of the pump beam. As the pump beam is a pulse of radiation comprising a plurality of frequencies, then a pulse of radiation which has frequencies in the range from 25 GHz to 100 THz is emitted from optically non-linear member 15. In this particular example, the optically non-linear member is ZnTe, in the (110) cryptallograph orientation.

ZnTe is chosen because it has good (second order) non-linear optical properties and also has negligible intrinsic birefringence. The relevance of the intrinsic birefringence of the optically non-linear member will be described with relation to the detection process.

The beam of emitted radiation 21 exits the optically non-linear member 15 and impinges on curved THz mirror 23. Curved mirror 23 is configured to reflect light from the optically non-linear member 15 onto second curved mirror 25 and from then onto sample 27.

The radiation is then reflected 29 from sample 27 back onto second curved mirror 25 which, in turn, reflects the reflected THz radiation 29 onto curved mirror 23. Curved mirror 23 is provided with a hole to allow a combination of the reflected radiation 29 with the probe beam 9. The reflected radiation 29 and the probe beam 9 are combined for detection.

The probe beam 9 is divided from beam 2 using polarising beam splitter 5. The probe beam 9 is passed through a modulator 31 which applies a modulation frequency $f_2$ onto the probe beam 9. This modulation frequency $f_2$ is added to the probe beam so that the probe beam can be distinguished. The modulation frequency $f_2$ is different to the modulation frequency $f_1$ applied to the pump beam 7.

The modulated probe beam 9 is then fed into variable optical delay line 33 via mirror 34. The delay line comprises a moveable cube mirror 37 which reflects radiation onto mirror 39. The position of cube mirror 37 can be varied so that the length of the optical path between mirror 35 and mirror 39 can be varied as required. By varying the length of the optical path, the arrival time of the probe beam at the detection crystal 15 is varied relative to the reflected THz beam 29 allowing the electric field of the reflected beam to be measured versus time.

The probe beam 9 is reflected from mirror 39 as it exits the optical delay line 33 and is passed through lens 41 and second polariser 43. Second polariser 43 serves to linearly polarise the probe beam 9 for recombination with the detected radiation. The second polariser 43 is a vertical polariser. In the instance when there is a non-negligible intrinsic birefringence in the detection crystal, element 43 in a variable waveplate compensator, that applies a pre-bias to the probe beam. Such a pre-bias results in the probe beam being vertically polarised after passing through member 15, in the absence of a THz beam 29. The vertically polarised beam then passes through an aperture 45 in the back of curved mirror 23. Curved mirror 23 is used to collect the reflected THz radiation 29 from the sample. Therefore, the reflected THz radiation 29 is combined with probe beam 9 via curved mirror 23. The reflected radiation and the probe beam are then focused onto optically non-linear member 15. It should be noted that the reflected THz radiation has a modulation frequency of $f_1$ and the probe radiation 9 has a modulation frequency of $f_2$. The mixing of the reflected THz radiation 29 and the probe radiation 9 provides probe radiation with a modulation frequency of $f_1-f_2$ after passing through member 15.

The presence of the reflected THz radiation 29 induces a temporary birefringence in the optically non-linear member 15. The reflected THz radiation 29 and the probe beam 9 are passed through the optically non-linear member together. This birefringence causes a rotation in the polarisation of the vertically probe beam 9. The degree of rotation is dependent on the THz radiation. Therefore, measurement of the change in the polarisation angle of the probe beam allows information about the reflected THz and hence the sample to be determined. In other words, the optically non-linear member 15 is used to extract information from the reflected THz beam 29 and encode this information on the probe beam 9.

The probe beam 9 then exits the optically non-linear member 15 and is directed onto polarising beam splitter 19. The polarising beam splitter 19 is configured to reflect radiation of the probe beam 9 with orthogonal (horizontal) polarisation with respect to the incident probe beam (coming from the optically non-linear member 15) onto horizontal third polariser 47. The horizontal polariser 47 is aligned so that it is crossed with vertical polariser 43. The horizontal polariser 47 will not pass vertically polarised radiations. Therefore, if the polarisation of the probe beam has not been rotated in the optically non-linear member (i.e. if there is no THz detected) then the horizontal polariser 47 serves to completely block the probe beam. However, if the rotation of the polarisation of the probe beam has been rotated, then horizontal polariser 47 will allow through the horizontal component of the probe beam 9. The magnitude of the horizontal component of the probe beam 9 is dependent on the degree of rotation of polarisation and hence, the reflected THz radiation.

The photodetector 49 is then used to detect the magnitude of the radiation which is transmitted through third polariser 47. The photodetector 49 is configured to detect that the modulation frequency $f_1-f_2$ detecting at this frequency will allow the elimination of any spurious pump beam, reflected THz beam etc which has reached the detector, this is the modulation frequency $f_1$ and also allows the elimination of any probe beam $f_2$ which has not been combined with the reflected THz radiation 29.

The pump beam 7 is pulsed, so THz radiation is only periodically emitted from the optically non-linear member 15. The apparatus is configured so that the reflected THz beam and the probe beam arrive at the optically non-linear member 15, when emission is not taking place. The length of the optical path of the probe beam 9 needs to be carefully chosen to ensure that the radiation pulses of the probe beam reach the optically non-linear member 15 at the correct time.

Figure 2:
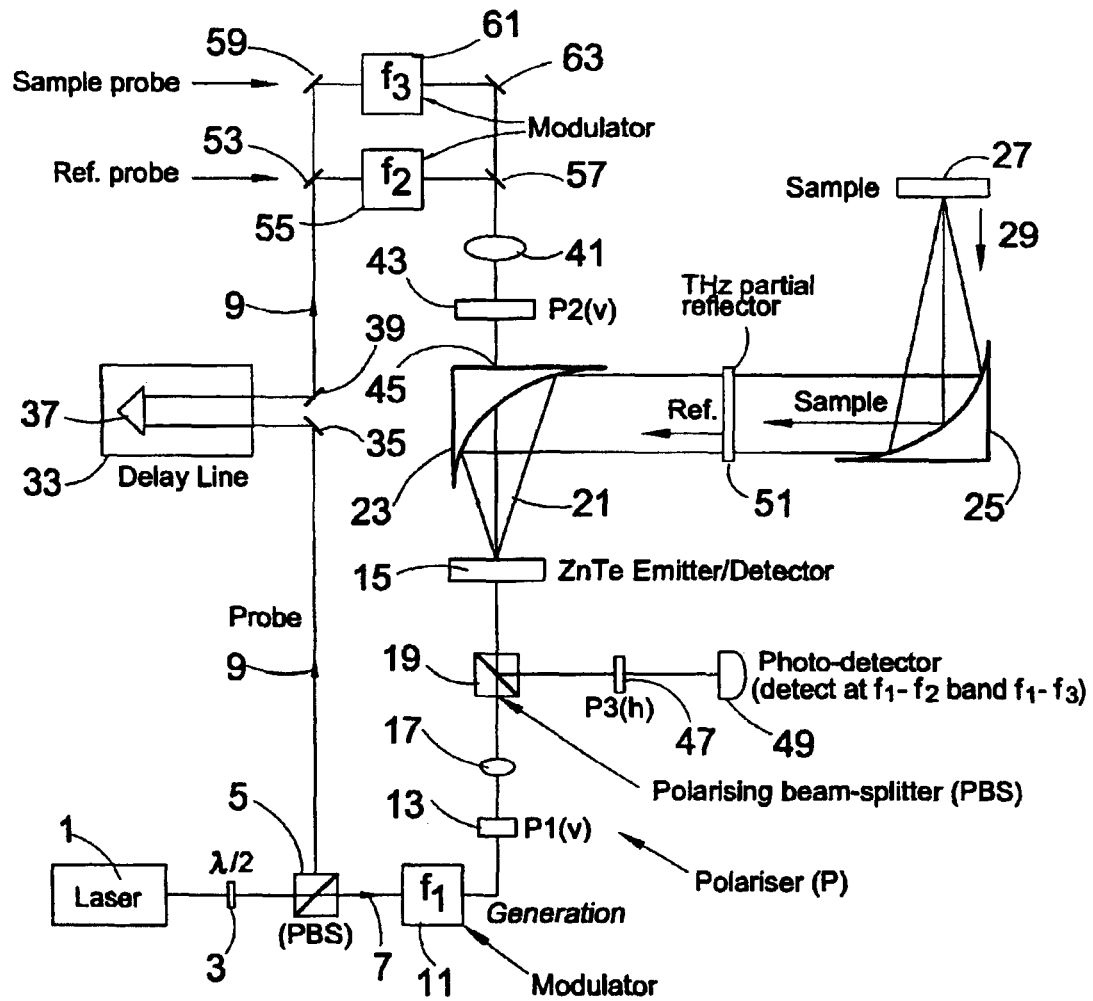
FIG. 2 shows a further variation on the apparatus of FIG. 1.

FIG. 2 shows a variation on the system of FIG. 1. To avoid unnecessary repetition, like numerals will be used to denote like features. The difference between FIG. 1 and FIG. 2 is that the system of FIG. 2 allows the measurement of a reference THz beam.

This is achieved by providing partial THz reflector 51 between mirrors 23 and 25. Therefore part of the THz emitted radiation which is reflected from mirror 23 does not reach sample 25 but is reflected back onto mirror 23 for recombination with probe beam. Typically this would be 1% of the total THz beam.

In FIG. 1, the pulses of radiation in the probe beam 9 are configured to reach the optically non-linear member at the same time as the pulse of reflected THz radiation 29 from the sample. To be able to also detect THz radiation from the mirror 51, it is necessary for the probe beam to be split into a sample probe beam and a reference probe beam. These two probe beams are configured to reach the optically non-linear member with the radiation reflected from the sample 27 and the mirror 51 respectively. In FIG. 1, the probe beam is modulated with frequency $f_2$. However, it would be difficult to distinguish between the signals from THz reflector S1 and from sample 27. Therefore, the reference probe beam is provided with a modulation f2 and the sample probe beam with modulation frequency $f_3$.

Probe beam 9 is derived from laser 1 using beam splitter 5. The probe beam 9 is directed onto mirror 35 from polarising beam splitter 5. There is no modulation applied to the probe beam before the probe beam enters optical delay line 33. Optical delay line 33 functions in exactly the same way to vary the path length between mirrors 35 and 39 as described with reference to FIG. 1. Mirror 39 reflects the probe beam 9 onto beam splitter 53. Beam splitter 53 reflects some of the probe beam 9 into modulator 55 which applies modulation frequency $f_2$ onto the probe beam 9. The modulated probe beam 9 is then reflected from mirror 57 onto curved mirror 23 for recombination with the radiation reflected from mirror 37. The other part of the probe beam 9 passes through beam splitter 53 and is reflected from mirror 59 into modulator 61 which provides the probe beam with the modulation frequency $f_3$. This probe beam is then reflected via mirror 63 through beam splitter 57 and onto curved mirror 23 where it can be combined with the radiation which is reflected from the sample.

The radiation is pulsed radiation. Therefore, radiation which is reflected from the sample and reflector 51 arrives at the optically non-linear member 15 at different times. The probe beam with the modulation $f_3$ is designed to arrive at the optically non-linear member at the same time as the radiation which is reflected from sample 27. The radiation with the modulation $f_2$ has a different optical path to travel and is designed to reach the optically non-linear member with the radiation which is reflected from THz reflector 51. Therefore, the THz radiation from the sample and the reflector 51 can be easily distinguished.

Figure 3:
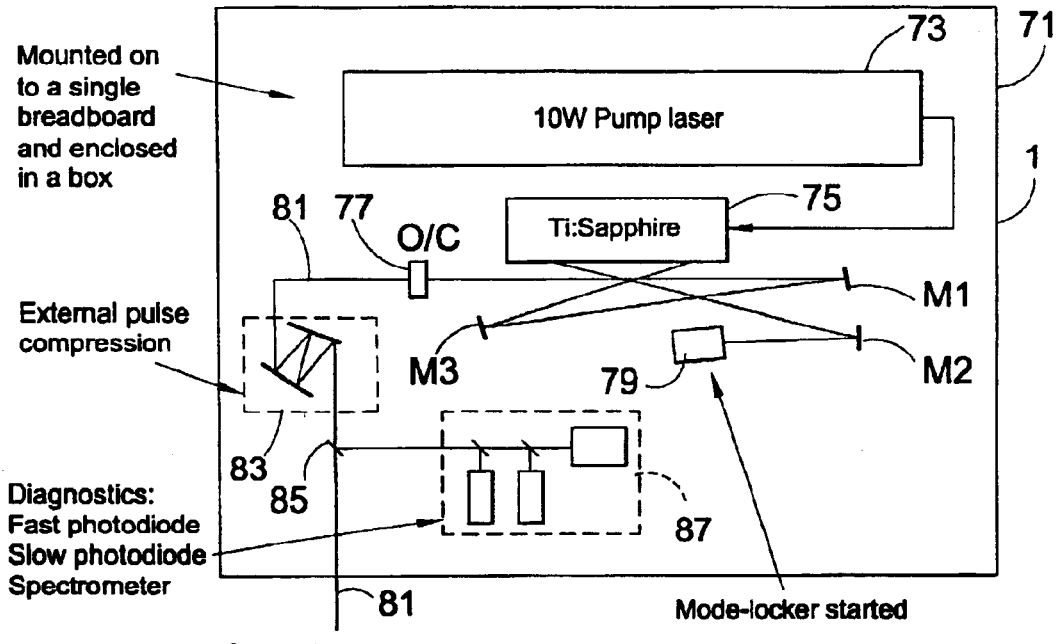
FIG. 3 shows an apparatus which can be used to generate an input beam for use with either of the systems of FIG. 1 or FIG. 2.

FIG. 3 shows an example of laser 1. The laser comprises a housing 71 which is located on a single bread board. The laser comprises a 10 watt pump laser 73 which is located within the housing 71. This provides an input signal to Ti:Sapphire oscillator 75 which outputs a beam into the lasing cavity which is defined by Ti:Sapphire oscillator 75, mirrors M1, M2, M3, output coupler 77 and mode locked starter 79. Mode locked starter 79 serves to initiate the mode locking of the output of the laser. Output coupler 77 serves to output some of the laser beam incident on the output coupler 77. However, it also serves as a reflector as it is important to continually supply the oscillator with radiation of the desired output frequency in order to achieve lasing.

The laser beam 81 from output coupler 77 is then fed into pulse compressor 83. Pulse compressor 83 comprises two mirrors with chirped dielectric coatings which are used to bounce the light back and forth to shorten the pulse in the time domain, before exiting pulse compressor 83. The output from pulse compressor 83 is passed through beam splitter 85 which passes most of the beam 81 out of the housing 71. The beam splitter 85 splits off part of the beam into diagnostic box 87. Diagnostic box 87 comprises well known diagnostics such as a fast photo diode, slow photo diode and spectrometer in order to measure the characteristics of the outputted beam.

Figure 4:
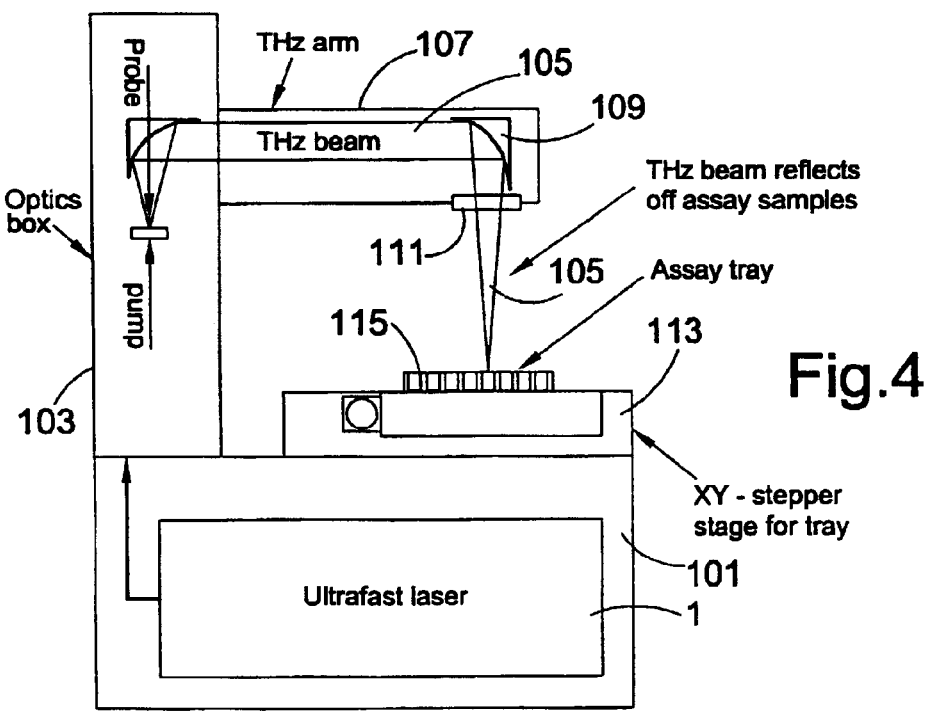
FIG. 4 shows a further embodiment of the present invention.

FIG. 4 shows a schematic example of the system of FIGS. 1 and 2 used for analysis of samples in an Assay tray. The details of the system are largely those described with reference to FIGS. 1, 2 and 3. The system comprises a base 101 which houses ultrafast laser 1 as described with reference to FIG. 3. The output from ultrafast laser 1 is split into probe and pump beams in optics box 103. Optics box 103 stands vertically on base 101. Optics box 103 will be described with reference to FIG. 5. Optics box 103 emits a THz beam 105 which is channelled down THz arm 107. A curved mirror 109 is provided at the end of THz arm 107, curved mirror 109 channels the THz beam 105 through window 111 and down onto the sample stage 113. Sample stage 113 is located above base 101. The sample stage 113 is provided with an X-Y stepper motor which allows the sample to be moved into two orthogonal directions perpendicular to that of the direction of THz beam 105 which is incident on the sample. The sample is an Assay tray which comprises a plurality of test tubes 115. The X-Y stepper motor for this stage can be configured so that the THz beam can be moved from test tube to test tube.

In a manner as described for sample 27 in FIGS. 1 and 2, THz radiation is reflected from the sample. This reflected radiation is passed through mirror 111 back into THz arm 107. The reflected radiation is then collected by curved mirror 109 and directed into optics box 103.

Figure 5:
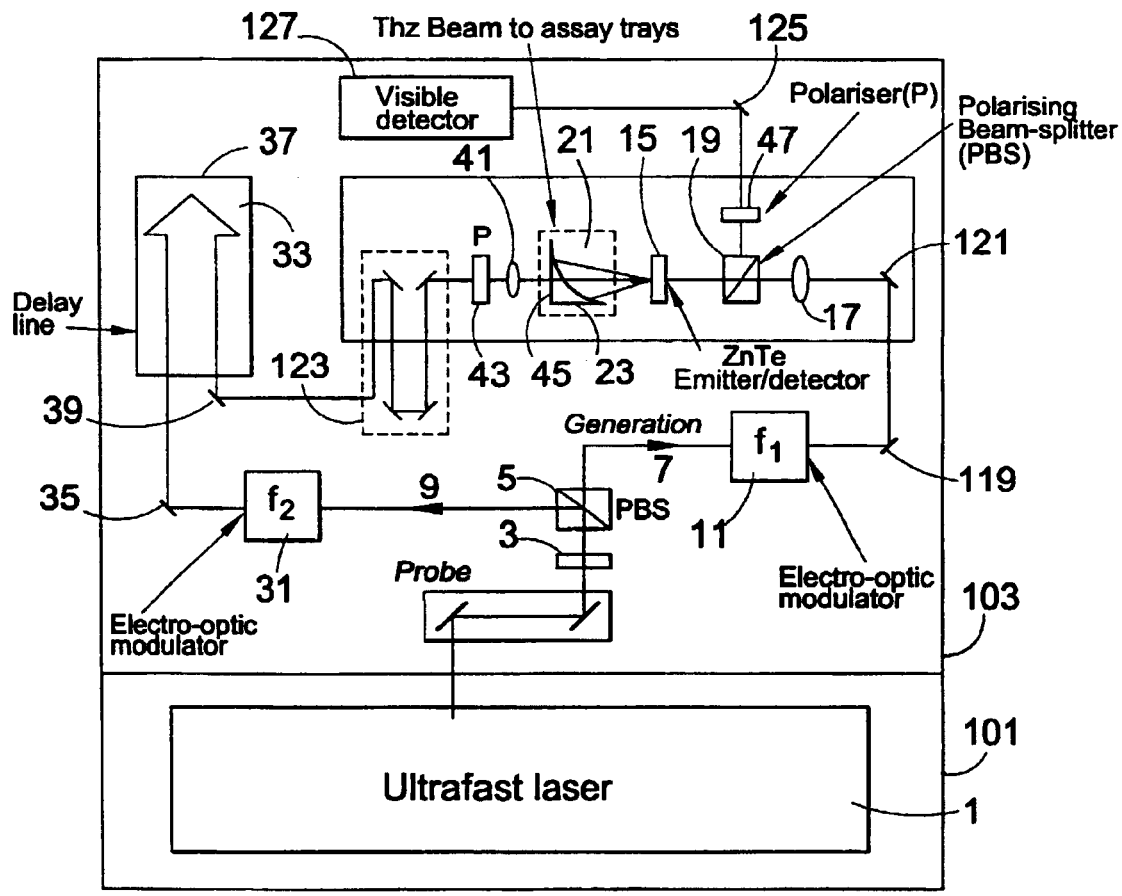
FIG. 5 shows an example of an optical arrangement which can be used with the embodiment of FIG. 4.

FIG. 5 shows a view of the system of FIG. 4 from the left-hand side (as looking at FIG. 4).

The optics box 103 is located above base 101. The output beam from ultrafast laser 1 is fed into box 103. In the same manner as described for FIG. 1, the output is then fed through halfway plate 3 and onto polarising beam splitter 5 which splits the beam into a pump beam 7 and a probe beam 9. The pump beam 7 is fed into modulator 11 which provides a modulation frequency $f_1$ on the pump beam 7.

Pump beam 7 is then directed via mirrors 119 and 121 through lens 17 and onto polarising beam splitter 19. In the manner as described for FIG. 1, polarising beam splitter 19 transmits the pump beam 7 into optically non-linear member 15. Polarising beam splitter 19 serves to linearly polarise the transmitted pump beam 7. The THz beam 21 which is emitted from the optically non-linear member onto curved mirror 23 which serves to direct the THz beam 21 down THz arm 107 (not shown) is described with reference to FIG. 4. Further, this mirror 23 also serves to collect the reflected THz from the sample. The probe beam 9 is fed through modulator 31 which serves to put a modulation of frequency $f_2$ onto the probe beam 9. The beam is then fed via mirror 35 into optical delay line 33 as described with reference to FIG. 1.

Mirror 39 then directs the beam onto mirror assembly 123. Mirror assembly 123 simply serves to increase the optical path of the probe beam. The delay line can obviously increase or decrease the length of the optical path of the probe beam. However, the delay line can be configured to change the path within a small range for example, if the length of the pulse is 1–3 ps, the delay line moves 0.3–1.0 mn. The main consideration, however, is the spectral resolution. For example, 500 GHz corresponds to an optical delay of 20 ps, corresponding in turn to 6 mm of motion. In a small system, it is important that the probe pulse and the reflected THz reach the optically non-linear member 15 at the same time.

Once the beam exits mirror assembly 123, it is directed onto polariser 43 which via lens 41 focuses the beam onto aperture 45 in curved mirror 23. The curved mirror 23 serves to combine the reflected radiation with the probe beam 9 as described with reference to both FIGS. 1 and 2. The combined radiation passes through optically non-linear member 15 where the THz beam (if present) serves to rotate the polarisation of the probe beam 9. This is then fed onto polarising beam splitter 19 which directs the beam (without changing its polarisation) onto third polariser 47. Third polariser 47 is crossed with polariser 43 such that it will block any radiation which has not had its polarisation vector rotated. The radiation transmitted through polariser 47 is then directed via mirror 125 onto visible light detector 127.

Figure 6:
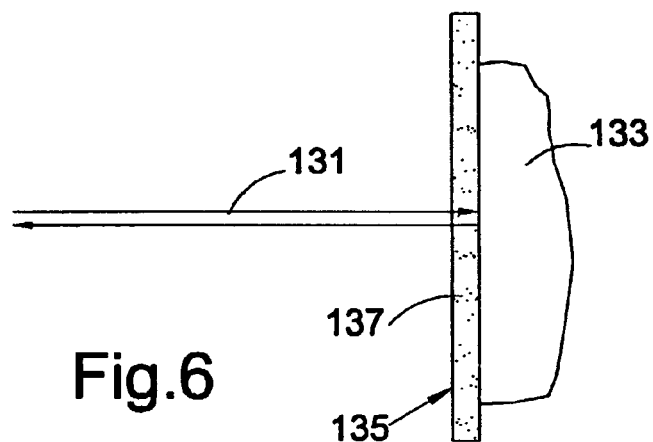
FIG. 6 shows a part of an imaging apparatus in accordance with an embodiment of the present invention.

The above example has used Assay trays as the sample. However, the present invention is of considerable use in looking at biological samples. FIG. 6 shows a schematic arrangement for such a proposed use. The THz beam 131 is directed and reflected from sample 133 as previously explained.

A problem with reflection measurements is the provision of a flat surface, if the surface is not flat, then there is a chance that the reflected radiation will be reflected at an angle to the sample and will be outside the range of the detector. In FIG. 6, there is a window member 135 provided adjacent the sample. If the sample is a biological sample, then the sample 133 can be pushed against window 135 which allows a flat surface for achieving the reflection measurements. It should be noted that ideally, the window 135 should have a refractive index which is very close to that of the sample. Window 135 is formed of a silica gel with silicon or germanium particles 137 suspended in the gel. The provision of the silica or germanium particles allows the refractive index of the window to be tuned exactly to that of the sample.

What is claimed is:

1. An apparatus for investigating a sample, the apparatus comprising:
    an emitter for irradiating the sample with a beam of emitted electromagnetic radiation; and
    a detector for detecting radiation reflected from the sample,
    wherein there is an optically non-linear member which functions as both an active part of the emitter and an active part of the detector, said emitter and detector using the same region of the optically non-linear member.

2. An apparatus according to claim 1, wherein the optically non-linear member is configured to emit a beam of radiation having at least one frequency in the range from 25 GHz to 100 THz.

3. An apparatus according to claim 1, wherein the emitted beam is a pulsed beam and comprises a plurality of frequencies.

4. An apparatus according to claim 1, wherein the optically non-linear member is configured to emit the emitted beam in response to irradiation by an input beam having a different frequency to that of the emitted beam.

5. An apparatus according to claim 4, wherein the optically non-linear member is configured such that irradiation of the member by radiation reflected from the sample induces a birefringence in the member and the birfringence is detected by irradiating the opticaly non-linear member with a probe beam and detecting the change in the rotation of the polarisation of the probe beam caused by the non-linear member ad wherein the input in the input beam and the probe beam are taken from the same source.

6. An apparatus according to claim 1, wherein the optically non-linear member is configured such that irradiation of the member by radiation reflected from the sample induces a birefringence in the member.

7. An apparatus according to claim 6, wherein the birefringence produced in the optically non-linear member by the reflected radiation is detected by irradiating the optically non-linear member by a probe beam and detecting the change in the rotation of the polarisation of the probe beam caused by the non-linear member.

8. An apparatus according to claim 7, the apparatus comprising means for combining the reflected radiation with the probe beam prior to irradiating the optically non-linear member.

9. An apparatus according to claim 7, wherein the apparatus further comprises means to apply a modulation frequency to the probe beam.

10. An apparatus according to claim 1, the apparatus being configured such that the emitted beam is emitted from the non-linear member and the reflected radiation is incident on the non-linear member.

11. An apparatus according to claim 1, further comprising means for detecting a reference signal, said means comprising a reflection member which is configured to partially reflect the emitted radiation, located between the non-linear member and the sample.

12. An apparatus according to claim 1, further comprising means to apply a modulation frequency to the emitted radiation.

13. An apparatus according to claim 1, said apparatus being configured to measure a liquid sample, said apparatus comprising means to obtain a spectra from a liquid sample and means to hold a liquid sample.

14. An apparatus according to claim 13, wherein said apparatus is configured to measure a plurality of individual liquid samples, each of said individual liquid samples being located in a test tube and said test tubes being located in an Assay tray.

15. An apparatus according to claim 14, wherein said apparatus is configured to irradiate a plurality of liquid samples at a time and detect radiation from a plurality of samples.

16. An apparatus according to claim 14, the apparatus comprising means to step the plurality of samples through the beam of emitted radiation, such that each liquid sample can be analysed.

17. An apparatus for according to claim 1, further comprising a window member which is transparent to said emitted and reflected radiation, said window member being located adjacent and in contact with the sample.

18. An apparatus according to claim 17, wherein the refractive index of the window member is substantially equal to that of the sample.

19. An apparatus according to claim 18, wherein the window member comprises a gel having a suspension of silicon or germanium particles.

20. A method of investigating a sample, the method comprising:
    irradiating a sample with a beam of emitted electromagnetic radiation which is emitted from a non-linear crystal;
    detecting the radiation which is reflected from the sample using the said nonlinear crystal as an active part of the detector;
    wherein the steps of irradiating and detecting the reflected radiation use the same region of the non-linear crystal.

* * * * *